(12) United States Patent
Takemura et al.

(10) Patent No.: US 6,469,023 B1
(45) Date of Patent: Oct. 22, 2002

(54) HETEROCYCLIC SPIRO-DERIVATIVE

(75) Inventors: Makoto Takemura, Tokyo (JP); Youichi Kimura, Tokyo (JP); Hitoshi Ohki, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 08/875,863

(22) PCT Filed: Feb. 6, 1996

(86) PCT No.: PCT/JP96/00248

§ 371 (c)(1),
(2), (4) Date: Aug. 7, 1997

(87) PCT Pub. No.: WO96/24593

PCT Pub. Date: Aug. 15, 1996

(30) Foreign Application Priority Data

Feb. 7, 1995 (JP) .............................................. 7-19480
Jun. 19, 1995 (JP) ............................................. 7-150791

(51) Int. Cl.[7] ........................ A61K 31/44; A01N 43/42; C07D 471/02
(52) U.S. Cl. ...................................... 514/300; 546/123
(58) Field of Search ........................... 514/300; 546/123

(56) References Cited

FOREIGN PATENT DOCUMENTS

| CA | 2023217 | * | 2/1991 | |
| EP | 341 493 A2 | | 11/1989 | |
| EP | 413455 | * | 2/1991 | |
| EP | 550016 | * | 7/1993 | |
| EP | 0 550 016 A1 | | 7/1993 | ......... C07D/401/04 |
| EP | 0 550 025 A1 | | 7/1993 | ......... C07D/209/54 |
| EP | 593 766 A1 | | 4/1994 | |
| JP | 57-72981 | | 5/1982 | ......... C07D/471/04 |
| JP | 60-260577 | | 12/1985 | ......... C07D/471/04 |
| JP | 64-56673 | | 3/1989 | ......... C07D/403/04 |
| JP | 3-86875 | | 4/1991 | ......... C07D/401/04 |

OTHER PUBLICATIONS

Jerry March, "Advanced Organic Chemistry—Reactions, Mechanisms, and Structure", 4th Edition, @ 1992, pp. 120–127.*

* cited by examiner

Primary Examiner—Richard L. Raymond
Assistant Examiner—Tamthom N. Truong
(74) Attorney, Agent, or Firm—Sughrue Mion, PLLC

(57) ABSTRACT

The present invention provides an antibacterial compound useful as medicines, animal drugs, fisheries drugs or antibacterial preservatives and to an antibacterial agent or preparation which contains the same, more particularly a compound which possesses high safety and excellent activity against a broad range of bacterial species including quinolone-resistant strains. A quinolone derivative of the following formula (I) which has a group derived from the heterocyclic spiro-compound at the 7-positioned $R^2$ and the halogenocyclopropyl group at the $N_1$-position, prefereably a compound of pure isomer, and an antibacterial agent containing the derivative compound.

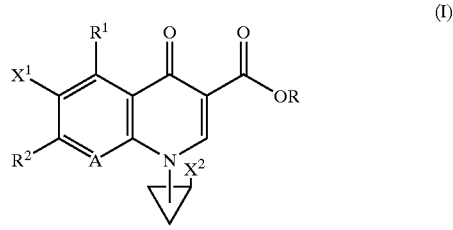

(I)

7 Claims, No Drawings

HETEROCYCLIC SPIRO-DERIVATIVE

TECHNICAL FIELD

This invention relates to an antibacterial compound useful as medicines, animal drugs, fisheries drugs or antibacterial preservatives and to an antibacterial agent or preparations which contains the same.

BACKGROUND ART

Though quinolone derivatives having a 1-amino-5-azabispiro[2.4]heptyl group are disclosed in European Patent Publication Nos. 550,016A and 550,025A, nothing is known about the quinolone derivative of the present invention having a 1-amino-5-azabispiro[2.4]heptyl group at the 7-position and a halogenocyclopropyl group at the 1-position, which comprises a single isomer.

Synthetic quinolone antibacterial agents having not only antibacterial activities but also excellent biological distribution such as oral absorbability, distribution into organs, urinary excretion ratio and the like have been found in recent years, and a number of such compounds are now supplied to the clinical field as chemotherapeutic agents effective against various infectious diseases. However, the presence of bacterial strains having low sensitivity to these drugs has been increasing in recent years in the clinical field. Also, like the case of *Staphylococcus aureus* (MRSA) having less sensitivity against β-lactam antibiotics, strains having low sensitivity to synthetic quinolone antibacterial agents are increasing even among strains which are resistant to other drugs than synthetic quinolone antibacterial agents. In consequence, development of drugs having more higher efficacy has been called for in the clinical field.

DISCLOSURE OF INVENTION

The present inventors thought that structures of the 7-and 1-position substituent groups played important role for the antibacterial activity, efficacy and safety of synthetic quinolone antibacterial agents. In consequence, the present inventors have conducted intensive studies to obtain a compound having high antibacterial activity against a broad range of bacteria including quinolone-resistant strains, and as a result, have found that a quinolone derivative having at its 7-position a substituent group derived from a heterocyclic spiro-compound whose the hetero atom is nitrogen shows strong antibacterial activity against Gram-negative and Gram-positive bacteria, particularly quinolone-resistant bacteria including MRSA, and that not only the antibacterial activity but also excellent efficacy and safety can be obtained by a quinolone derivative in which the 1-position is substituted with a halogenocyclopropyl group, particularly fluorocyclopropyl group.

In the quinolone derivative of the present invention, only a pair of enantiomers is present attributable to the halogenocyclopropane ring moiety at the 1-position even in the absence of stereoisomerism in the substituents at the other positions. This is originated from a stereochemical relationship between pyridonecarboxylic acid moiety and halogen atom on the cyclopropane ring. When isomers formed in this way are racemic, such derivative is a mixture of antipodes and could be administered as a medicine as such.

On the other hand, when stereoisomerism is also present at the other positions, particularly at the 7-position substituent, in addition to the stereoisomerism of the halogenocyclopropene ring moiety, the quinolone derivative involves diastereomers, meaning that 4 or more stereoisomers are present. Since the mixture of diastereomers is a mixture of compounds having different physical properties, it is difficult to administer the mixture as a medicine.

The present inventors have made intensive efforts to obtain a quinoline compound consisting of a single stereoisomer even in the case of a 1-(1,2-cis-2-halogenocyclopropyl)-substituted quinolone derivative which involves diastereomers.

As the results, the present inventors have succeeded in obtaining each enantiomer of cis-2-fluorocyclopropylamine as a pure compound. The present inventors have also succeeded in obtaining each of the fluorocyclopropane ring configuration-originated enantiomers of the quinolone derivative as a compound of pure isomer, from the pure cis-2-fluorocyclopropylamine. The present inventors have also succeeded in obtaining each isomer of a heterocyclic spiro-compound having an asymmetric carbon atom and a nitrogen hetero atom, as a pure compound.

The success in obtaining such quinolone derivative and heterocyclic spiro-compound having a nitrogen atom as a hetero atom, both useful as intermediates, has rendered possible synthesis of an optically active quinolone derivative as a single diastereomer.

Thereafter, the present invention has been accomplished on the basis of a finding that the novel quinolone derivative of the present invention which has a group derived from the heterocyclic spiro-compound at the 7-position and the halogenocyclopropyl group at the 1-position is a compound of high safety and shows excellent activity against a broad range of bacterial species including quinolone-resistant strains.

Accordingly, the present invention relates to an $N_1$-(halogenocyclopropyl)-substituted pyridonecarboxylic acid derivative represented by formula (I):

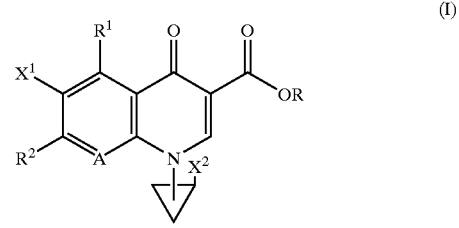

wherein $X^1$ represents a halogen atom or a hydrogen atom;

$X^2$ represents a halogen atom;

$R^1$ represents a hydrogen atom, a hydroxyl group, a thiol group, a halogenomethyl group, an alkyl group having 1 to 6 carbon atoms, an alkoxyl group having 1 to 6 carbon atoms, an amino group (said amino group may have a substituent selected from the group consisting of a formyl group, an alkyl group having 1 to 6 carbon atoms and an acyl group having 2 to 5 carbon atoms, and the amino group may be dialkyl-substituted when the substituents are alkyl groups which may be the same or different from each other);

$R^2$ represents a group having a structure derived from a heterocyclic spiro-compound, represented by formula (II):

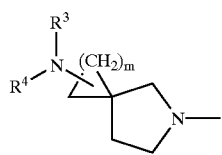

(II)

wherein $R^3$ and $R^4$ independently represent a hydrogen atom or an alkyl group having 1 to 6 carbon atoms and m is an integer of 1 or 2;

A represents a nitrogen atom or a partial structure of formula (III):

(III)

wherein $X^3$ represents a hydrogen atom, a halogen atom, a cyano group, an alkyl group having 1 to 6 carbon atoms, a halogenomethyl group, an alkoxyl group having 1 to 6 carbon atoms, a halogenomethoxyl group, an amino group (said amino group may have more than one substituents selected from the group consisting of a formyl group, an alkyl group having 1 to 6 carbon atoms or an acyl group having 2 to 5 carbon atoms, and the amino group may be dialkyl-substituted when the substituents are alkyl groups which may be the same or different from each other); and R represents a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group;

or a salt thereof.

The present invention also relates to the aforementioned compound or a salt thereof, in which the halogenocyclopropyl group in the formula (I) is a 1,2-cis-2-halogenocyclopropyl group.

The present invention also relates to the aforementioned compound or a salt thereof, in which $R^2$ in the formula (I) is a stereochemically pure substituent.

The present invention also relates to the aforementioned compound or a salt thereof, in which the halogenocyclopropyl group in the formula (I) is a stereochemically pure substituent.

The present invention also relates to the aforementioned compound or a salt thereof, in which the halogenocyclopropyl group is a (1R,2S)-2-halogenocyclopropyl group.

The present invention also relates to the aforementioned compound or a salt thereof, in which $X^2$ is a fluorine atom.

The present invention also relates to an antibacterial agent which contains the aforementioned compound of the formula (I) or a salt thereof as an active ingredient.

Other objects and advantages of the present invention will be made apparent as the description progresses.

The following describes substituents of the compound of the present invention represented by the formula (I).

When each of $X^1$, $X^2$ and $X^3$ is a halogen atom, $X^1$ and $X^2$ are most preferably a fluorine atom and $X^3$ is preferably a fluorine atom or a chlorine atom.

$R^1$ is a hydrogen atom, a hydroxyl group, a thiol group, a halogenomethyl group, an alkyl group having 1 to 6 carbon atoms, an alkoxyl group having 1 to 6 carbon atoms, or an amino group which may have more than one substituents selected from a formyl group, an alkyl group having 1 to 6 carbon atoms or an acyl group having 2 to 5 carbon atoms, and the amino group may be dialkyl-substituted when the substituents are alkyl groups which may be the same or different from each other.

As for the substituent $R^1$, the alkyl group includes straight or branched-chain alkyl groups having 1 to 6 carbon atoms, preferably methyl, ethyl, n-propyl or isopropyl group.

As the halogen atom of the halogenomethyl group, a fluorine atom is particularly preferred and the number of the atom may be 1 to 3. Preferred examples of the halogenomethyl group include a fluoromethyl group and a difluoromethyl group.

When $R^1$ is an amino group, a hydroxyl group or a thiol group, these groups may be protected with ordinary protective groups.

Examples of such protective groups include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl and the like, ethers such as methoxymethyl, tertiary buyoxymethyl, tetrahydropyranyl, 2,2,2-trichloroethoxymethyl and the like, and silyl groups such as trimethylsilyl, isopropyldimethylsilyl, tertiarybutyldimethylsilyl, tribenzylsilyl, tertiary butyldiphenylsilyl and the like.

Of these protective groups, ethers and silyl groups may be used preferably as those for a hydroxyl group and a thiol group, and other protective groups can be used as those for any one of an amino group, a hydroxyl group and a thiol group.

$X^3$ is a hydrogen atom, a halogen atom, a cyano group, an alkyl group having 1 to 6 carbon atoms, a halogenomethyl group, an alkoxyl group having 1 to 6 carbon atoms, a halogenomethoxyl group, or an amino group which may have more than one substituents selected from a formyl group, an alkyl group having 1 to 6 carbon atoms or an acyl group having 2 to 5 carbon atoms, and the amino group may be dialkyl-substituted when the substituent group is alkyl groups which may be the same or different from each other.

As for the substituent $X^3$, the alkyl group includes straight or branched-chain alkyl groups having 1 to 6 carbon atoms, preferably methyl, ethyl, n-propyl or isopropyl group.

As the halogen atom of the halogenomethyl group, a fluorine atom is particularly preferred and the number of the atom may be 1 to 3. Preferred examples of the halogenomethyl group include a fluoromethyl group and a difluoromethyl group.

The alkoxyl group may have 1 to 6 carbon atoms and is preferably a methoxyl group.

As the halogen atom of the halogenomethoxyl group, a fluorine atom is particularly preferred and the number of the atom may be 1 to 3.

When A is a partial structure represented by the formula (III),

(III)

preferred combination of $R^1$ and $X^3$ is that $R^1$ is an amino group, a hydrogen atom, a hydroxyl group or an alkyl group having 1 to 6 carbon atoms and $X^3$ is an alkyl group having 1 to 6 carbon atoms, an alkoxyl group having 1 to 6 carbon atoms, a halogen atom, a halogenomethoxyl group or a hydrogen atom.

In more preferred combination, $R^1$ is an amino group, a hydrogen atom, a hydroxyl group or a methyl group and $X^3$ is a methyl group, a methoxyl group, a fluorine atom, a chlorine atom, a difluoromethoxyl group or a hydrogen atom.

In most preferred combination, $R^1$ is an amino group, a hydrogen atom, a hydroxyl group or a methyl group and $X^3$ is a methyl group or a methoxyl group.

To these $R^1$ and $X^3$ groups, $X^1$ and $X^2$ are preferably fluorine atoms.

$R^2$ is a group represented by the following formula (II),

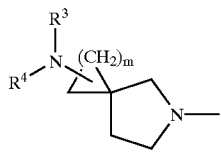

(II)

which is derived from a heterocyclic spiro-compound represented by the following formula

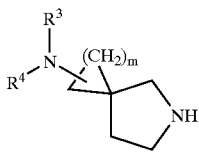

(though a case in which the pyrrolidine ring nitrogen is hydrogen-substituted is shown herein, it may be substituted with other substituent such a s a protective group of a nitrogen atom). This group has an amino group as a substituent on the spiro-ring of methylene chain. Since this moiety resembles to have an alicyclic cyclic amine structure, the present inventors think that this structure is taking an important role for the appearance of the excellent properties of the compound of the present invention.

The term "heterocyclic spiro-compound" as used herein means a compound which has a structure formed by the replacement of carbon atom constructing a cyclic structure of an alicyclic Spiro compound by a hetero atom such as a nitrogen atom or the like.

In the above formula, $R^3$ and $R^4$ independently represent a hydrogen atom or an alkyl group having 1 to 6 carbon atoms and m is an integer of 1 or 2. The alkyl group may be either straight or branched chain having 1 to 6 carbon atoms, and is preferably a methyl group.

In a preferred combination of $R^3$ and $R^4$, one of $R^3$ and $R^4$ is a hydrogen atom and the other is an alkyl group having 1 to 6 carbon atoms.

In a more preferred combination, one of $R^3$ and $R^4$ is hydrogen atom and the other is a methyl group or an ethyl group.

Also, m is an integer of 1 or 2.

The connection of the $R^2$ to the 7-position of the quinolone nucleus may be effected most preferably on the ring-member nitrogen atom, but also on a ring-member carbon atom of $R^2$.

When stereoisomerism is present in $R^2$ and the quinolone nucleus compound is allowed to react with a mixture of stereoisomers of the heterocyclic spiro-compound which is the source of the substituent represented by the formula (II), the formed quinolone derivative becomes a mixture of diastereomers due to the 1,2-cis-2-halogenocyclopropyl group at the 1-position. Therefore, when stereoisomerism is present in $R^2$, it is desirable to allow only one of the isomers of the heterocyclic spiro-compound to react with the quinolone nucleus compound.

When $R^2$ is introduced into the 7-position of the quinolone and at least one of $R^3$ and $R^4$ of the heterocyclic spiro-compound is a hydrogen atom, it may be subjected to the reaction as a compound in which $R^3$ or $R^4$ is not a hydrogen atom but an ordinary protective group.

Examples of such protective groups include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl and the like, alkylsulfonyl groups or halogenoalkylsulfonyl groups such as methanesulfonyl, trifluoromethanesulfonyl and the like, and arylsulfonyl groups such as benzenesulfonyl, toluenesulfonyl and the like.

Next, the halogenocyclopropyl group at the $N_1$-position is described.

Examples of the halogen atom to be substituted include a fluorine atom and a chlorine atom, of which a fluorine atom is particularly preferred.

With regard to the stereochemical environment in this moiety, it is particularly desirable that the halogen atom and the pyridonecarboxylic acid moiety take a cis configuration against the cyclopropane ring.

Enantiomeric isomers are formed only by this cis-2-halogenocyclopropyl moiety at 1-position independent of the stereoisomerism of substituents at other positions, particularly $R^2$ at the 7-position. Strong antibacterial activity and high safety have been found in each of these isomers.

When the compound (I) of the present invention has a structure in which diastereomers exist and such a compound of the present invention is administered to human and animals, it is desirable to administer a compound comprising a single diastereomer. The term "comprising a single diastereomer" means not only a case in which the other diastereomer is entirely absent but also a case of chemically pure degree. In other words, the other diastereomer may be contained in such a degree that it does not exert influences upon physical constants and physiological activities.

Also, the term "stereochemically pure" means that, when a compound has a plurality of isomeric species due to its asymmetric carbon atom, the compound is composed of only one of these species. The term "pure" in this case can also be considered in the same manner as the aforementioned case of diastereomer.

The pyridonecarboxylic acid derivative of the present invention may be used as its free form, or as an acid addition salt or a salt of its carboxyl group. Examples of the acid addition salt include inorganic acid salts such as hydrochloride, sulfate, nitrate, hydrobromide, hydroiodide, phosphate and the like and organic acid salts such as acetate, methanesulfonate, benzenesulfonate, toluenesulfonate, citrate, maleate, fumarate, lactate and the like.

The salt of carboxyl group may be any one of inorganic and organic salts such as lithium salt, sodium salt, potassium salt and the like alkali metal salts, magnesium salt, calcium salt and the like alkaline earth metal salts, ammonium salt, triethylamine salt, N-methylglucamine salt, tris(hydroxymethyl)aminomethane salt and the like.

In addition, these free form, acid addition salts and carboxyl group salts of the pyridonecarboxylic acid derivative may be present as hydrates.

On the other hand, quinolone derivatives, in which the carboxylic acid moiety is an ester, are useful as synthetic intermediates and prodrugs. For example, alkyl esters, benzyl esters, alkoxyalkyl esters, phenylalkyl esters and phenyl esters are useful as synthetic intermediates.

Examples of esters to be used as prodrugs are those which are easily hydrolyzed in the living body to form a free carboxylic acid, such as acetoxymethyl ester, pivaloiloxymethyl ester, ethoxycarbonyl ester, choline ester, dimethylaminoethyl ester, 5-indanyl ester, phthalidinyl ester and oxoalkyl esters such as 5-alkyl-2-oxo-1,3-dioxol-4-yl methyl ester, 3-acetoxy-2-oxobutyl ester and the like.

The compound of the present invention represented by the formula (I) can be produced by various methods. In a preferred example, it can be produced by allowing the heterocyclic spiro-compound of formula $R^2$—H (wherein $R^2$ is as defined in the foregoing as the formula (II) in relation to the formula (I), except that $R^3$ and/or $R^4$ may form a protective group Rx of the nitrogen atom), or an acid addition salt thereof to react with a compound (quinolone nucleus compound) represented by formula (IV):

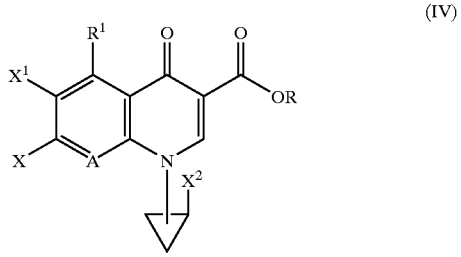

(IV)

wherein X is a group which serves as a leaving group, for example, a fluorine atom, a chlorine atom, a bromine atom, an alkylsulfonyl group having 1 to 3 carbon atoms or an arylsulfonyl group such as a benzenesulfonyl group, a toluenesulfonyl group or the like; R is the same R defined in the formula (I) or a group represented by formula (V):

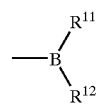

(V)

wherein each of $R^{11}$ and $R^{12}$ is a fluorine atom or a lower alkylcarbonyloxy group;
and $X^1$, $X^2$, $R^1$ and A are as defined in the formula (I).

The protective group Rx of the nitrogen atom is any group generally used in this field, and examples of such protective group include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl and the like, alkylsulfonyl or halogenoalkylsulfonyl groups such as methanesulfonyl, trifluoromethanesulfonyl and the like, and arylsulfonyl groups such as benzenesulfonyl, toluenesulfonyl and the like.

When R is an alkyl group having 1 to 6 carbon atoms, an alkoxymethyl group having 2 to 7 carbon atoms or an aralkyl group composed of an alkylene group having 1 to 6 carbon atoms and phenyl group, the compound of interest represented by the formula (I) can be obtained by carrying out conversion of the resulting carboxylic acid esters into the corresponding carboxylic acid under acidic or basic conditions which are common in the hydrolysis of esters and, if necessary, removing the protective group under corresponding suitable conditions.

When R in the compound of the formula (IV) is a group represented by the aforementioned formula (V), its conversion into the corresponding carboxylic acid can be achieved after carrying out a substitution reaction with the heterocyclic spiro-compound by treating the product with an acidic or basic compound.

Substitution reaction of the heterocyclic spiro-compound with the compound of formula (IV) can be carried out with or without a solvent. When a solvent is used, it may be inert under the reaction conditions. Examples of suitable solvents include dimethyl sulfoxide, pyridine, acetonitrile, ethanol, chloroform, dimethylformamide, dimethylacetamide, N-methylpyrrolidone, tetrahydrofuran, water, 3-methoxybutanol and mixtures thereof.

The reaction can be carried out at a temperature of generally from room temperature to 200° C., preferably from 25 to 150° C. The reaction time is about 30 minutes to 48 hours, and the reaction is completed generally in a time of from about 30 minutes to 2 hours.

It is advantageous to carry out the reaction in the presence of an acid acceptor which includes inorganic bases such as carbonates or hydrogencarbonates of alkali metals or alkaline earth metals and organic basic compounds such as triethylamine, pyridine and the like.

A heterocyclic spiro-compound in which the hetero atom is nitrogen can be produced, for example, by the following method. That is, 1-benzyloxycarbonyl-3-hydroxypyrrolidine is allowed to react with oxalyl chloride and dimethyl sulfoxide to yield 1-benzyloxycarbonyl-3-pyrrolidone. This compound is allowed to react with a solution prepared from zinc, titanium tetrachloride and dibromomethane, thereby obtaining 1-benzyloxycarbonyl-3-methylenepyrrolidine. This compound is allowed to react with ethyl diazoacetate in the presence of a rhodium catalyst to yield 5-benzyloxycarbonyl-3-ethoxycarbonyl-5-azaspiro[2.4]heptane. Though this compound is a mixture of diastereomers, these isomers can be separated from each other by a silica gel column chromatography or a high performance liquid chromatography. Each of the thus obtained isomers is allowed to react with a base in an ordinary method to effect ester hydrolysis, thereby 5-benzyloxycarbonyl-5-azaspiro[2.4]heptane-1-carboxylic acid is obtained. When this compound is subjected to Curtius reaction in the presence of tert-butanol, it can be converted at once into protected 5-benzyloxycarbonyl-1-tert-butoxycarbonylamino-5-azaspiro[2.4]heptane. This reaction can be carried out easily when diphenylphosphorylazide is used, but synthesis of the intermediate azide is not limited thereto and any ordinary synthetic method can be employed. Though each of the thus obtained compounds is a racemic compound comprising a pair of diastereomers, it was found that optical isomers of each compound can be separated by a high performance liquid chromatography using a chiral column. When the benzyloxycarbonyl group is removed from the thus obtained single isomer of 5-benzyloxycarbonyl-1-tert-butoxycarbonyl-amino-5-azaspiro[2.4]heptane by catalytic hydrogenation in an ordinary method, 1-tert-butoxycarbonylamino-5-azaspiro[2.4]heptane comprising a single optical isomer is obtained.

Cis-2-fluorocyclopropylamine comprising a single isomer, which is suitable for the synthesis of the compound of formula (I) that comprises a single isomer, can be synthesized for example in accordance with the method disclosed in JP-A-2-231475 (the term "JP-A" as used herein means an "unexamined published Japanese patent application"). The compound of formula (IV) comprising a single isomer can be synthesized from the thus obtained optically active cis-2-fluorocyclopropylamine derivative, for example, in accordance with the method disclosed in JP-A-2-231475.

Since the compound of the present invention shows strong antibacterial activities, it can be used as medicines for human, animals and fishes or preservatives of agricultural chemicals and food.

When the compound of the present invention is used as a medicine in human, its dose may be in the range of from 50 mg to 1 g, preferably from 100 mg to 300 mg, per adult per day.

When used in animals, its dose varies depending on the purpose of administration (treatment or prevention), kind and size of each animal to be treated, kind of infected pathogenic bacterium and degree of the infection, but is generally in the range of from 1 to 200 mg, preferably from 5 to 100 mg, per day per 1 kg of animal body weight.

The daily dose may be used once a day or divided into 2 to 4 doses per day. If necessary, the daily dose may exceed the range recited above.

Since the compound of the present invention is active upon a broad range of microorganisms which cause various types of infectious diseases, it can heal, prevent or alleviate diseases caused by these pathogenic microorganisms.

Examples of bacteria and bactericidal microorganisms sensitive to the compound of the present invention include the genus Staphylococcus, *Streptococcus pyogenes*, hemolytic streptococcus, enterococcus, pneumococcus, the genus Peptostreptococcus, gonococcus, *Escherichia coli*, the genus Citrobacter, the genus Shigella, Friedlander's bacillus, the genus Enterobacter, the genus Serratia, the genus Proteus, *Psuedomonas aeruginosa, Haemophilus influenzae*, the genus Acinetobacter, the genus Campylobacter, *Chlamydia trachomatis* and the like.

Examples of diseases caused by these pathogenic microorganisms include folliculitis, furuncle, carbuncle, erysipelas, phlegmon, lymphangitis, felon, subcutaneous abscess, hidradenitis, concentrated acne, infectious atheroma, perirectal abscess, mastitis, superficial secondary infections such as of injury, burn injury, operative wound and the like, pharyngolaryngitis, acute bronchitis, tonsillitis, chronic bronchitis, bronchiectasis, diffuse panbronchiolitis, secondary infection of chronic respiratory disease, pneumonia, pyelonephritis, cystitis, prostatitis, epididymitis, gonococcal urethritis, non-gonococcal urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, otitis media, sinusitis, periodontium inflammation, pericrown inflammation, jaw inflammation, peritonitis, endocarditis, sepsis, meningitis, dermal infection and the like.

The compound of the present invention is also effective against various microorganisms which cause infectious diseases in animals, such as those which belong to the genera Escherichia, Salmonella, Pasteurelle, Haemophilus, Bordetella, Staphylococcus, Mycoplasma and the like. Illustrative examples of such diseases include coli bacillosis, pullorum disease, chicken paratyphoid fever, fowl cholera, infectious coryza, staphylococcal infection, mycoplasma infection and the like in the case of birds, coli bacillosis, salmonellosis, pasteurellosis, haemophilus infection, atrophic rhinitis, exudative epidermis, mycoplasma infection and the like in the case of swine, coli bacillosis, salmonellosis, hemorrhagic sepsis, mycoplasma infection, bovine pleuropneumonia, bovine mastitis and the like in the case of cattle, coli sepsis, salmonella infection, hemorrhagic sepsis, uterine empyema, cystitis and the like in the case of dogs, and exudative pleurisy, cystitis, chronic rhinitis, haemophilus infection, kitten diarrhea, mycoplasma infection and the like in the case of cats.

The antibacterial agent, which comprises the compound of the present invention, can be prepared making use of various commonly used pharmaceutical drug preparation methods by selecting appropriate dosage form corresponding to each administration method. Examples of the dosage form of the antibacterial agent which contains the compound of the present invention as the active component include oral preparations such as tablets, powders, capsules, solutions, syrups, elixirs, oily or aqueous suspensions and the like.

When used as injections, the preparation may contain a stabilizing agent, an antiseptic agent and a solubilizing agent. As occasion demands, a solution which may contain such auxiliary substances may be packed in containers and made into a solid preparation by freeze-drying or the like means to be dissolved again before its use. Also, a container may be packed with a single dose or multiple doses.

The antibacterial agent of the present invention may also be made into preparations for external use such as solutions, suspensions, emulsions, ointments, gels, creams, lotions, sprays and the like.

Solid preparations contain pharmaceutically acceptable additives together with the active compound and can be produced by mixing these additives optionally selected, for example, from fillers, extenders, binders, disintegrating agents, solubilizing agents, moistening agents, lubricants and the like.

Liquid preparations include solutions, suspensions, emulsions and the like which may contain suspending agents, emulsifying agents and the like as additives.

When the compound of the present invention is applied to animals, it may be effected, for example, by a method in which the compound is orally administered directly or after adding it to feed, by another method in which the compound is made into a solution and then orally administered directly or after adding it to drinking water or feed or by injection.

When the compound of the present invention is administered to animals, it can be made optionally into powders, fine subtilaes, dissolvable powders, syrups or injections in accordance with usually used techniques in this field.

Examples of the formulation of pharmaceutical preparations are shown below.

Preparation Example 1 (Capsules)

| | |
|---|---:|
| Compound of Inventive Example 2 | 100.0 mg |
| Corn starch | 23.0 mg |
| CMC calcium | 22.5 mg |
| Hydroxymethylcellulose | 3.0 mg |
| Magnesium stearate | 1.5 mg |
| Total | 150.0 mg |

Preparation Example 2 (Solution)

| | |
|---|---:|
| Compound of Inventive Example 2 | 1–10 g |
| Acetic acid or sodium hydroxide | 0.5–2 g |
| Ethyl paraoxybenzoate | 0.1 g |
| Purified water | 88.9–98.4 g |
| Total | 100 g |

Preparation Example 3 (Powder for Feed Mixing use)

| | |
|---|---:|
| Compound of Inventive Example 2 | 1–10 g |
| Corn starch | 98.5–89.5 g |
| Soft silicic anhydride | 0.5 g |
| Total | 100 g |

BEST MODE FOR CARRYING OUT INVENTION

EXAMPLES

The following Inventive and Reference Examples are provided to further illustrate the present invention, but not by way of limitation. The antibacterial activity of optically active compounds of interest was tested in accordance with the standard method designated by Japan Society of Chemotherapy. The results are shown in Table 1 as MIC ($\mu$g/ml).

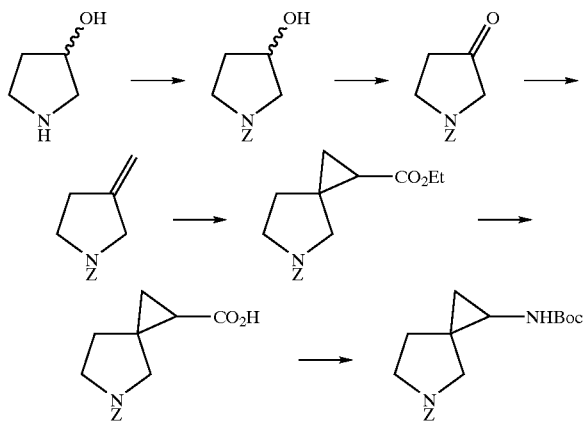

Example A

1-Benzyloxycarbonyl-3-pyrrolidone

A dichloromethane (40 ml) solution of 16.58 ml (233.6 mmol) of dimethyl sulfoxide was added dropwise to a dichloromethane (200 ml) solution of 10.19 ml (116.8 mmol) of oxalyl chloride at −78° C., and the mixture was stirred for 10 minutes at the same temperature. To the reaction solution was added dropwise a solution of 23.50 g of literary known 1-benzyloxycarbonyl-3-hydroxypyrrolidine in 200 ml of dichloromethane at −78° C., followed by 60 minutes of stirring at the same temperature. This solution was mixed with 74.02 ml (531.1 mmol) of triethylamine at −78° C., and stirred for 60 minutes at the same temperature and then at room temperature for 60 minutes. After completion of the reaction, 500 ml of water was added dropwise to the reaction solution, and the organic layer was separated. The aqueous layer was washed with dichloromethane (100 ml×2), and combined organic layer was washed with saturated brine (300 ml×1). After drying the organic layer over sodium sulfate, the solvent was evaporated. The resulting residue was subjected to a silica gel column chromatography to yield 20.1 g (86%) of the title compound as an oily product from the eluate of n-hexane:ethyl acetate=1:1.

$^1$H-NMR (400 MHz, CDCl$_3$) δ: 2.58–2.62 (2H, m), 3.82–3.87 (4H, m), 5.18 (2H, s), 7.30–7.37 (5H, m).

Example B

1-Benzyloxycarbonyl-3-methylenepyrrolidine

A 8.44 ml (77 mmol) portion of titanium tetrachloride was added dropwise to 350 ml of tetrahydrofuran solution containing 36.6 g (600 mmol) of zinc at 0° C., and the mixture was stirred for 60 minutes at the same temperature. To the reaction solution cooled at 0° C. was added dropwise 24.32 ml (350 mmol) of dibromomethane dissolved in 100 ml of tetrahydrofuran, followed by stirring at room temperature overnight. To the reaction solution was added dropwise tetrahydrofuran (100 ml) solution of 15.35 g (70 mmol) 1-benzyloxycarbonyl-3-pyrrolidone at room temperature, followed by 50 minutes of stirring at the same temperature. After completion of the reaction, the reaction solution was mixed with 500 ml of 1 N hydrochloric acid and extracted with ethyl acetate (500 ml×2), and the organic layer was washed with saturated brine (300 ml×1). After drying the organic layer over anhydrous sodium sulfate, the solvent was evaporated. The resulting residue was subjected to a silica gel column chromatography to yield 12.4 g (82%) of the title compound as an oily product from the eluate of n-hexane:ethyl acetate=2:1.

$^1$H-NMR (400 MHz, CDCl$_3$) δ: 2.57 (2H, br s), 3.55 (2H, dd, J=7.82, 16.12 Hz), 4.01 (2H, d, J=5.86 Hz), 4.97 (2H, 2 s), 5.14 (2H, s), 7.29–7.38 (5H, m).

Example C

5-Benzyloxycarbonyl-3-ethoxycarbonyl-5-azaspiro [2.4]-heptane (a), (b)

A 8.2 g (37.7 mmol) portion of 1-benzyloxycarbonyl-3-methylenepyrrolidine was dissolved in 300 ml of cyclohexane and mixed with 100 mg of rhodium acetate dimer. To the thus prepared mixture was added dropwise a dichloromethane solution of 0.5 mM ethyl diazoacetate spending 20 hours while heating under reflux. After completion of the dropwise addition, the solvent was evaporated and the resulting residue was subjected to a silica gel column chromatography to obtain 4.12 g (36%) of the title compound (a) and 4.05 g (35%) of the title compound (b) each as an oily product from the eluate of n-hexane:ethyl acetate= 2:1. At the same time, 2.3 g of the starting material was recovered.

Isomer (a)

$^1$H-NMR (400 MHz, CDCl$_3$) δ: 1.10–1.18 (1H, m), 1.26 (3H, t, J=7.33 Hz), 1.29–1.33 (1H, m), 1.74–1.82 (1H, m), 2.00–2.08 (2H, m), 3.28–3.58 (4H, m), 4.14 (2H, dd, J=6.84, 14.16 Hz), 5.13 (2H, 2 s), 7.31–7.37 (5H, m).

Isomer (b)

$^1$H-NMR (400 MHz, CDCl$_3$) δ: 1.13–1.18 (1H, m), 1.25 (3H, t, J=6.84 Hz), 1.29–1.35 (1H, m), 1.72–1.79 (2H, m), 1.94–1.97 (1H, m), 3.52–3.58 (4H, m), 4.10–4.16 (2H, m), 5.12 (2H, 2 s), 7.29–7.37 (5H, m).

Example D

5-Benzyloxycarbonyl-5-azaspiro[2.4]heptane-1-carboxylic Acid (a)

A 4.12 g (13.6 mmol) portion of 5-benzyloxycarbonyl-3-ethoxycarbonyl-5-azaspiro[2.4]heptane (a) was dissolved in 20 ml of ethanol, cooled in an ice bath and mixed with 20.4 ml of 1 N sodium hydroxide aqueous solution. The resulting mixture was stirred at room temperature for 3.5 hours. After completion of the reaction, the reaction solution was acidified by adding 10% citric acid aqueous solution, ethanol was evaporated and then the resulting water layer was extracted with ethyl acetate (50 ml×4). The organic layers were combined and dried over sodium sulfate. By evaporating the solvent, 2.86 g (76%) of the title compound was obtained as an oily product.

$^1$H-NMR (400 MHz, CDCl$_3$) δ: 1.19–1.27 (1H, m), 1.35–1.38 (1H, m), 1.77–1.85 (1H, m), 2.02–2.16 (2H, m), 3.29–3.45 (2H, m), 3.56–3.60 (2H, m), 5.13 (2H, 2 s), 7.30–7.35 (5H, m).

Example E

5-Benzyloxycarbonyl-5-azaspiro[2.4]heptane-1-carboxylic Acid (b)

A 4.05 g (13.3 mmol) portion of 5-benzyloxycarbonyl-3-ethoxycarbonyl-5-azaspiro[2.4]heptane (b) was dissolved in 20 ml of ethanol, cooled in an ice bath and mixed with 20.0 ml of 1 N sodium hydroxide aqueous solution. The resulting mixture was stirred at room temperature for 3.5 hours. After completion of the reaction, the reaction solution was acidified by adding 10% citric acid aqueous solution, ethanol was evaporated and then the resulting water layer was extracted with ethyl acetate (50 ml×4). The organic layers were combined and dried over sodium sulfate. By evaporating the solvent, 3.07 g (84%) of the title compound was obtained as an oily product.

$^1$H-NMR (400 MHz, CDCl$_3$) δ: 1.21–1.27 (1H, m), 1.35–1.39 (1H, m), 1.79–1.80 (1H, m), 1.97–2.04 (2H, m), 3.52–3.61 (4H, m), 5.14 (2H, 2 s), 7.30–7.36 (5H, m).

Example F

5-Benzyloxycarbonyl-1-tert-butoxycarbonylamino-5-azaspiro-[2.4]heptane (a) and HPLC Separation (1-a; 2-a)

A 2.86 g (10.39 mmol) portion of 5-benzyloxycarbonyl-5-azaspiro[2.4]heptane-1-carboxylic acid (a) was dissolved in 50 ml of tert-butanol. To this solution were added dropwise 4.29 g (15.6 mmol) of diphenylphosphoric acid azide and 2.90 ml (20.8 mmol) of triethylamine in that order at room temperature, followed by 18 hours of heating under reflux. After completion of the reaction, the solvent was evaporated and the resulting residue was subjected to a silica gel column chromatography to yield 2.0 g (55%) of the title compound as an oily product from the eluate of n-hexane:ethyl acetate=2:1.

This product was separated into stereoisomers (1-a) and (2-a) by subjecting it to an chiral column-equipped HPLC.

Column: CHIRALPAK AD, 2 cm×25 cm

Mobile phase: n-hexane:isopropanol=75:25

Flow rate: 7.0 ml/min

Temperature: room temperature

Detection: UV (254 nm)

Retention times of the optical isomers are as follows.

Compound (1-a): 12 minutes

Compound (2-a): 14 minutes

Isomer (1-a), 860 mg (24%);

$^1$H-NMR (400 MHz, CDCl$_3$) δ: 0.60 (1H, br s), 0.95–1.03 (1H, m), 1.43 (9H, s), 1.87 (2H, br s), 2.59 (1H, br s), 3.32 (2H, d, J=11.7 Hz), 3.55–3.62 (2H1 m), 4.64 (1H, br s), 5.12 (2H, 2 s), 7.30–7.37 (5H, m).

Isomer (2-a), 1.01 g (28%);

$^1$H-NMR (400 MHz, CDCl$_3$) δ: 0.60 (1H, br s), 0.95–1.03 (1H, m), 1.43 (9H, s), 1.87 (2H, br s), 2.59 (1H, br s), 3.32 (2H, d, J=12.7 Hz), 3.55–3.62 (2H, m), 4.64 (1H, br s), 5.12 (2H, 2 s), 7.31–7.37 (5H, m).

Example G

5-Benzyloxycarbonyl-1-tert-butoxycarbonylamino-5-azaspiro[2.4]-heptane (b) and HPLC Separation (1-b; 2-b)

A 3.05 g (11.08 mmol) portion of 5-benzyloxycarbonyl-5-azaspiro[2.4]heptane-1-carboxylic acid (b) was dissolved in 55 ml of tert-butanol. To this solution were added dropwise 4.57 g (16.6 mmol) of diphenylphosphoric acid azide and 3.09 ml (22.1 mmol) of triethylamine in that order at room temperature, followed by 18 hours of heating under reflux. After completion of the reaction, the solvent was evaporated and the resulting residue was subjected to a silica gel column chromatography to yield 1.7 g (44%) of the title compound as an oily product from the eluate of n-hexane:ethyl acetate=2:1.

This product was separated into stereoisomers (1-b) and (2-b) by subjecting it to an chiral column-equipped HPLC.

Column: CHIRALPAK AD, 2 cm×25 cm

Mobile phase: n-hexane:ethanol=50:50 (v/v)

Flow rate: 5.0 ml/min

Temperature: room temperature

Detection: UV (254 nm)

Retention times of the optical isomers are as follows.

Compound (1-b): 19 minutes

Compound (2-b): 28 minutes

Isomer (1-b), 844 mg (22%);

$^1$H-NMR (400 MHz, CDCl$_3$) δ: 0.63 (1H, br s), 0.98 (1H, br s), 1.40 (9H, s), 1.72 (1H, br s), 1.89 (1H, br s), 2.51 (1H, br s), 3.27–3.39 (2H, m), 3.59 (2H, br s), 4.93 (1H, br s), 5.13 (2H, s), 7.30–7.38 (5H, m).

Isomer (2-b), 760 mg (20%);

$^1$H-NMR (400 MHz, CDCl$_3$) δ: 0.63 (1H, br s), 0.98 (1H, br s), 1.40 (9H, s), 1.72 (1H, br s), 1.90 (1H, br s), 2.51 (1H, br s), 3.28–3.40 (2H, m), 3.59 (2H, br s), 4.82 (1H, br s), 5.13 (2H, s), 7.29–7.36 (5H, m).

Inventive Example 1

5-Amino-7-[1-amino-5-azaspiro[2.4]heptan-5-yl]-6,
8-difluoro-1-[(1R,2S)-2-fluorocyclopropyl]-1,4-
dihydro-4-oxoquinoline-3-carboxylic Acid [Isomer I
(1-a)]

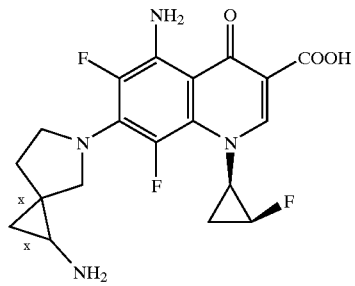

A 346 mg (1.00 mmol) portion of 5-benzyloxycarbonyl-1-tert-butoxycarbonylamino-5-azaspiro[2.4.]heptane (1-a) was dissolved in 30 ml of ethanol, and the solution was mixed with 350 mg of 10% palladium-carbon and subjected to 4 hours of hydrogenation under atmospheric pressure. After completion of the reaction, 10% palladium-carbon was removed by filtration and ethanol was evaporated. The thus obtained residue was suspended in 10 ml of acetonitrile, and the suspension was mixed with 210 mg (0.67 mmol) of 5-amino-6,7,8-trifluoro-1-[(1R,2S)-2-fluorocyclopropyl]1,4-dihydro-4-oxoquinoline-3-carboxylic acid and 0.93 ml (6.67 mmol) of triethylamine and heated under reflux for 24 hours. After evaporation of the solvent, the thus obtained residue was mixed with chloroform, washed with water, 10% citric acid aqueous solution and saturated brine in that order, and then dried over anhydrous sodium sulfate, subsequently evaporating the solvent. The thus obtained tert-butylcarbamate compound was mixed with 3 ml of concentrated hydrochloric acid, stirred at room temperature for 30 minutes, adjusted to pH 7.4 with sodium hydroxide aqueous solution and then extracted with chloroform, and the extract was dried over anhydrous sodium sulfate. After evaporation of the solvent, the resulting residue was recrystallized from ethanol to obtain 190 mg (69%) of the title compound.

Melting point: 195–198° C.; $[\alpha]_D^{25}$=+6.86, (c=0.495, 0.1 N sodium hydroxide aqueous solution); $^1$H-NMR (400 MHz, 0.1 N NaOD) δ: 0.48–0.51 (1H, m), 0.82–0.85 (1H, m), 1.51–1.57 (2H, m), 1.83–1.88 (1H, m), 2.00–2.07 (1H, m), 2.32–2.35 (1H, m), 3.39 (2H, s), 3.74 (3H, br s), 8.21 (1H, s). Elementary analysis for $C_{19}H_{19}N_4O_3F_3 \cdot \frac{1}{4}H_2O$: Calcd.: C, 55.27; H, 4.76; N, 13.57. Found : C, 55.46; H, 4.77; N, 13.43.

Inventive Example 2

5-Amino-7-[1-amino-5-azaspiro[2.4]heptan-5-yl]-6,
8-difluoro-1-[(1R,2S)-2-fluorocyclopropyl]-1,4-
dihydro-4-oxoquinoline-3-carboxylic Acid [Isomer I
(2-a)]

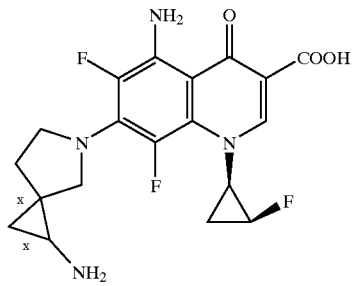

A 346 mg (1.00 mmol) portion of 5-benzyloxycarbonyl-1-tert-butoxycarbonylamino-5-azaspiro[2.4.]heptane (2-a) was dissolved in 30 ml of ethanol, and the solution was mixed with 350 mg of 10% palladium-carbon and subjected to 4 hours of hydrogenation under atmospheric pressure. After completion of the reaction, 10% palladium-carbon was removed by filtration and ethanol was evaporated. The thus obtained residue was suspended in 10 ml of acetonitrile, and the suspension was mixed with 210 mg (0.67 mmol) of 5-amino-6,7,8-trifluoro-1-[(1R,2S)-2-fluorocyclopropyl]1, 4-dihydro-4-oxoquinoline-3-carboxylic acid and 0.93 ml (6.67 mmol) of triethylamine and heated under reflux for 24 hours. After evaporation of the solvent, the thus obtained residue was mixed with chloroform, washed with water, 10% citric acid aqueous solution and saturated brine in that order, and then dried over anhydrous sodium sulfate, subsequently evaporating the solvent. The thus obtained tert-butylcarbamate compound was mixed with 3 ml of concentrated hydrochloric acid, stirred at room temperature for 30 minutes, adjusted to pH 7.4 with sodium hydroxide aqueous solution and then extracted with chloroform, and the extract was dried on anhydrous sodium sulfate. After evaporation of the solvent, the resulting residue was recrystallized from ethanol to yield 113 mg (41%) of the title compound.

Melting point: 216–219° C.; $[\alpha]_D^{25}$=+52.38, (c=0.399, 0.1 N sodium hydroxide aqueous solution); $^1$H-NMR (400 MHz, 0.1 N NaOD) δ: 0.47–0.49 (1H, m), 0.79–0.82 (1H, m), 1.50–1.58 (2H, m), 1.79–1.86 (1H, m), 1.98–2.04 (1H, m), 2.30–2.33 (1H, m), 3.36 (2H, s), 3.72 (3H, br s), 8.21 (1H, s). Elementary analysis for $C_{19}H_{19}N_4O_3F_3 \cdot \frac{1}{4}H_2O$: Calcd.: C, 55.27; H, 4.76; N, 13.57. Found : C, 55.39; H, 4.80; N, 13.37.

Inventive Example 3

5-Amino-7-[1-amino-5-azaspiro[2.4]heptan-5-yl]-6,
8-difluoro-1-[(1R,2S)-2-fluorocyclopropyl]-1,4-
dihydro-4-oxoquinoline-3-carboxylic Acid [Isomer I
(1-b)]

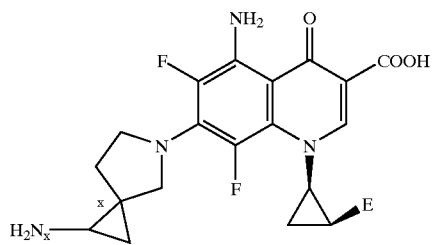

A 346 mg (1.00 mmol) portion of 5-benzyloxycarbonyl-1-tert-butoxycarbonylamino-5-azaspiro[2.4]heptane (1-b) was dissolved in 30 ml of ethanol, and the solution was mixed with 350 mg of 10% palladium-carbon and subjected to 4 hours of hydrogenation under atmospheric pressure. After completion of the reaction, 10% palladium-carbon was removed by filtration and ethanol was evaporated. The thus obtained residue was suspended in 10 ml of acetonitrile, and the suspension was mixed with 210 mg (0.67 mmol) of 5-amino-6,7,8-trifluoro-1-[(1R,2S)-2-fluorocyclopropyl]1, 4-dihydro-4-oxoquinoline-3-carboxylic acid and 0.93 ml (6.67 mmol) of triethylamine, and heated under reflux for 18 hours. After evaporation of the solvent, the thus obtained residue was mixed with chloroform, washed with water, 10% citric acid aqueous solution and saturated brine in that order, and then dried over anhydrous sodium sulfate, subsequently evaporating the solvent. The thus obtained tert-butylcarbamate compound was mixed with 5 ml of concentrated hydrochloric acid, stirred at room temperature for 30 minutes, adjusted to pH 7.4 with sodium hydroxide aqueous solution and then extracted with chloroform, and the extract was dried over anhydrous sodium sulfate. After evaporation of the solvent, the resulting residue was recrystallized from ethanol-ether to yield 198 mg (78%) of the title compound.

Melting point: 129–131° C.; $[\alpha]_D^{25}$=+51.76, (c=0.597, 0.1 N sodium hydroxide aqueous solution); $^1$H-NMR (400 MHz, 0.1 N NaOD) δ: 0.47–0.49 (1H, m), 0.86–0.89 (1H, m), 1.54–1.60 (2H, m), 1.74–1.85 (2H, m), 2.34–2.36 (1H, m), 3.57–3.83 (5H, m), 8.23 (1H, s). Elementary analysis for $C_{19}H_{19}N_4O_3F_3 \cdot \frac{3}{4}H_2O$: Calcd.: C, 54.09; H, 4.90; N, 13.28. Found : C, 53.84; H, 4.84; N, 13.05.

Inventive Example 4

5-Amino-7-[1-amino-5-azaspiro[2.4]heptan-5-yl]-6,
8-difluoro-1-[(1R,2S)-2-fluorocyclopropyl]-1,4-
dihydro-4-oxoquinoline-3-carboxylic Acid [isomer I
(2-b)]

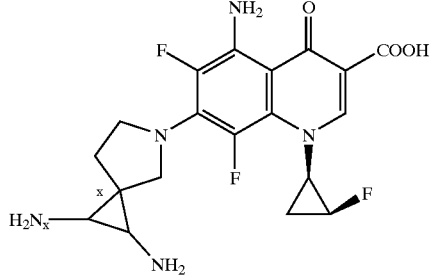

A 346 mg (1.00 mmol) portion of 5-benzyloxycarbonyl-1-tert-butoxycarbonylamino-5-azaspiro[2.4.]heptane (2-b) was dissolved in 30 ml of ethanol, and the solution was mixed with 350 mg of 10% palladium-carbon and subjected to 4 hours of hydrogenation under atmospheric pressure. After completion of the reaction, 10% palladium-carbon was removed by filtration and ethanol was evaporated. The thus obtained residue was suspended in 10 ml of acetonitrile, and the suspension was mixed with 210 mg (0.67 mmol) of 5-amino-6,7,8-trifluoro-1-[(1R,2S)-2-fluorocyclopropyl]1, 4-dihydro-4-oxoquinoline-3-carboxylic acid and 0.93 ml (6.67 mmol) of triethylamine, and heated under reflux for 18 hours. After evaporation of the solvent, the thus obtained residue was mixed with chloroform, washed with water, 10% citric acid aqueous solution and saturated brine in that order, and then dried over anhydrous sodium sulfate, subsequently evaporating the solvent. The thus obtained tert-butylcarbamate compound was mixed with 5 ml of concentrated hydrochloric acid, stirred at room temperature for 30 minutes, adjusted to pH 7.4 with sodium hydroxide aqueous solution and then extracted with chloroform, and the extract was dried over anhydrous sodium sulfate. After evaporation of the solvent, the resulting residue was recrystallized from ethanol-ether to yield 222 mg (81%) of the title compound.

Melting point: 180–181° C.; $[\alpha]_D^{25}$=+8.24, (c=0.46, 0.1 N sodium hydroxide aqueous solution); $^1$H-NMR (400 MHz, 0.1 N NaOD) δ: 0.45–0.47 (1H, m), 0.84–0.88 (1H, m), 1.51–1.59 (2H, m), 1.70–1.83 (2H, m), 2.32–2.35 (1H, m), 3.53–3.79 (5H, m), 8.22 (1H, s). Elementary analysis for $C_{19}H_{19}N_4O_3F_3 \cdot 1H_2O$: Calcd.: C, 53.52; H, 4.96; N, 13.14. Found : C, 53.32; H, 5.00; N, 13.00.

Inventive Example 5

5-Amino-7-[1-amino-5-azaspiro[2.4]heptan-5-yl]-6-fluoro-1-[(1R,2S)-2-fluorocyclopropyl]-8-methyl-1,4-dihydro-4-oxoquinoline-3-carboxylic Acid [isomer II (1-a)]

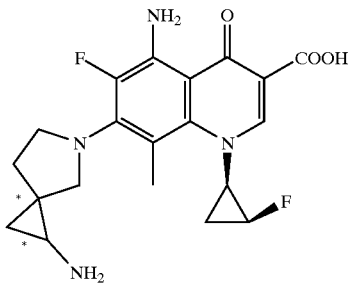

A 693 mg (2.00 mmol) portion of 5-benzyloxycarbonyl-1-tert-butoxycarbonylamino-5-azaspiro[2.4]heptane (1-a) was dissolved in 60 ml of ethanol, and the solution was mixed with 600 mg of 10% palladium-carbon and subjected to 2 hours of hydrogenation under atmospheric pressure. After completion of the reaction, 10% palladium-carbon was removed by filtration and ethanol was evaporated. The thus obtained residue was suspended in 6 ml of dimethyl sulfoxide, and the suspension was mixed with 312 mg (1.00 mmol) of 5-amino-6,7-difluoro-1-[(1R,2S)-2-fluorocyclopropyl]-8-methyl-1,4-dihydro-4-oxoquinoline-3-carboxylic acid and 2.00 ml (14.35 mmol) of triethylamine, and heated at 150 to 160° C. for 19 hours in a stream of nitrogen. After evaporation of the solvent, the thus obtained residue was mixed with chloroform, washed with water, 10% citric acid aqueous solution and saturated brine in that order, and then dried over anhydrous sodium sulfate, subsequently evaporating the solvent. The thus obtained tert-butylcarbamate compound was mixed with 5 ml of concentrated hydrochloric acid, stirred at room temperature for 20 minutes, washed with chloroform (50 ml×3), adjusted to pH 7.4 with sodium hydroxide aqueous solution and then extracted with chloroform, and the extract was dried over anhydrous sodium sulfate. After evaporation of the solvent, the resulting residue was purified by a preparative TLC (developed by the lower layer of chloroform:methanol:water 7:3:1) and recrystallized from ethanol-ether to yield 142 mg (35%) of the title compound.

Melting point: 118–120° C.; $[\alpha]_D^{24}$=−266.46, (c=0.486, 0.1 N sodium hydroxide aqueous solution); $^1$H-NMR (400 MHz, 0.1 N NaOD) δ: 0.46–0.48 (1H, m), 0.76–0.79 (1H, m), 1.07–1.18 (1H, m), 1.42–1.53 (1H, m), 1.78–1.84 (1H, m), 2.04–2.11 (1H, m), 2.28 (3H, s), 2.33–2.36 (1H, m), 3.01 (1H, d, J=9.28 Hz), 3.42 (2H, d, J=9.27 Hz), 3.73–3.76 (1H, m), 3.89–3.94 (1H, m), 7.81 (1H, s). Elementary analysis for $C_{20}H_{22}N_4O_3F_2 \cdot \frac{3}{4}H_2O$: Calcd.: C, 57.48; H, 5.67; N, 13.41. Found : C, 57.57; H, 5.62; N, 13.29.

Inventive Example 6

7-[1-Amino-5-azaspiro[2.4]heptan-5-yl]-6-fluoro-1-[(1R,2S)-2-fluorocyclopropyl]-1,4-dihydro-8-methyl-4-oxoquinoline-3-carboxylic Acid [Isomer III (1-a)]

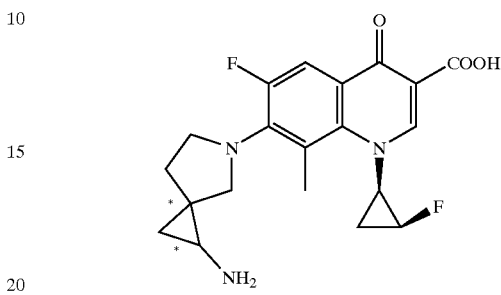

A 1.22 g (3.52 mmol) portion of 5-benzyloxycarbonyl-1-tert-butoxycarbonylamino-5-azaspiro[2.4]heptane (1-a) was dissolved in 100 ml of ethanol, and the solution was mixed with 1.00 g of 10% palladium-carbon and subjected to 3 hours of hydrogenation under atmospheric pressure. After completion of the reaction, 10% palladium-carbon was removed by filtration and ethanol was evaporated. The thus obtained residue was suspended in 5 ml of sulfolane, and the suspension was mixed with 690 mg (2 mmol) of 6,7-difluoro-1-[(1R,2S)-2-fluoro-1-cyclopropyl]-1,4-dihydro-8-methyl-4-oxoquinoline-3-carboxylic acid $BF_2$ chelate and 0.86 ml of triethylamine, and heated at 35° C. for 12 hours in a stream of nitrogen. After evaporation of triethylamine, the thus obtained residue was mixed with 10 ml of water and stirred at room temperature for 30 minutes. The thus formed crystals were washed with water, collected by filtration and dissolved in 25 ml of a mixture solvent of methanol:water= 9:1, and the resulting solution was mixed with 5 ml of triethylamine and heated under reflux for 1 hour. After evaporation of the solvent, the thus obtained residue was mixed with 5 ml of concentrated hydrochloric acid, stirred at room temperature f or 10 minutes and then washed with chloroform (5 ml×2). The reaction solution was adjusted to pH 7.3 with 20% sodium hydroxide aqueous solution and extracted with chloroform (30 ml×3). The extract was dried over sodium sulfate and the solvent was evaporated. The resulting residue was separated and purified by a preparative TLC (developed by the lower layer of chloroform:methanol:water=7:3:1) and recrystallized from ethanol-ether to yield 92 mg (12%) of the title compound.

Melting point: 103–109° C. $[\alpha]_D^{25}$=−185.14, (c=0.350, 0.1 N sodium hydroxide aqueous solution); $^1$H-NMR (400 MHz, 0.1 N NaOD) δ: 0.50 (1H, s), 0.82 (1H, m), 1.19–1.28 (1H, m), 1.58–1.6 (1H, m), 1.86–1.92 (1H, m), 2.10–2.12 (1H, m), 2.38 (1H, s), 2.52 (3H, s), 3.11 (1H, d, J=8.2 Hz), 3.42 (1H, d, J=8.3 Hz), 3.50 (1H, s), 3.75 (1H, s), 4.08 (1H, s), 7.68 (1H, d, J=13.68 Hz), 8.46 (1H, s). Elementary analysis for $C_{20}H_{21}N_3O_3F_2 \cdot \frac{1}{4}EtOH$: Calcd.: C, 61.42; H, 5.66; N, 10.48. Found : C, 61.69; H, 5.71; N, 10.19.

Inventive Example 7

7-[1-Amino-5-azaspiro[2.4]heptan-5-yl]-6-fluoro-1-
[(1R,2S)-2-fluorocyclopropyl]-1,4-dihydro-8-
methyl-4-oxoquinoline-3-carboxylic Acid [isomer
III (2-b)]

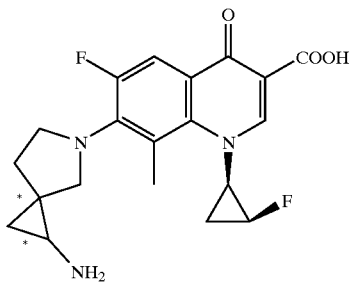

A 1.34 g (3.87 mmol) portion of 5-benzyloxycarbonyl-1-tert-butoxycarbonylamino-5-azaspiro[2.4]heptane (2-b) was dissolved in 50 ml of methanol, and the solution was mixed with 1.20 g of 5% palladium-carbon and subjected to 2 hours of hydrogenation under atmospheric pressure. After completion of the reaction, 5% palladium-carbon was removed by filtration and methanol was evaporated. The thus obtained residue was suspended in 7 ml of sulfolane, and the suspension was mixed with 690 mg (2.00 mmol) of difluoro{6,7-difluoro-1-[(1R,2S)-2-fluorocyclopropyl]-1,4-dihydro-8-methyl-4-oxoquinoline-3-carboxylate-O,O'}boron and 0.31 ml (2.20 mmol) of triethylamine and stirred at room temperature for 19 days in a stream of nitrogen. The reaction solution was mixed with 10% citric acid aqueous solution, and the thus precipitated solid was collected by filtration. After washing with water, this was dissolved in 100 ml of 10% aqueous methanol, mixed with 0.5 ml of triethylamine and heated under reflux for 18 hours. After evaporation of the solvent, the thus obtained residue was mixed with 10% citric acid aqueous solution and extracted with chloroform. The organic layer was dried over anhydrous sodium sulfate and the solvent was evaporated. The thus obtained residue was subjected to a silica gel column chromatography (chloroform:methanol=9:1) to yield a Boc compound. This was mixed with 10 ml of concentrated hydrochloric acid, stirred at 0° C. for 2 hours, adjusted to pH 12 with sodium hydroxide aqueous solution and then to pH 7.4 with hydrochloric acid. After extraction with chloroform, the organic layer was dried over anhydrous sodium sulfate and the solvent was evaporated. Thereafter, the resulting residue was recrystallized from ethanol to yield 319 mg (41%) of the title compound of interest.

$^1$H-NMR (400 MHz, 0.1 N NaOD) δ: 8.47 (1H, s), 7.70 (1H, d, J=14.16 Hz), 5.12–4,83 (1H, m), 4.13–4.07 (1H, m), 3.78–3.68 (1H, m), 3.64 (1H, d, J=9.76 Hz), 3.48–3.38 (1H, m), 3.34 (1H, d, J=9.77 Hz), 2.54 (3H, s), 2.38–2.32 (1H, m), 2.03–1.93 (1H, m), 1.80–1.70 (1H, m), 1.70–1.53 (1H, m), 1.34–1.18 (1H, m), 0.94–0.88 (1H, m), 0.53–0.47 (1H, m). Melting point: 206–208° C.; $[\alpha]_D^{25}$=−213.27, (c=0.407, 0.1 N NaOH); Elementary analysis for $C_{20}H_{21}F_2N_3O_3$; Calcd.: C, 61.69; H, 5.44; N, 10.79. Found : C, 61.53; H, 5.49; N, 10.73.

Inventive Example 8

5-Amino-7-[1-amino-1-azaspiro[2.4]hept-5-yl]-6-fluoro-1-[(1R,2S)-2-fluorocyclopropyl]-1,4-dihydro-8-methyl-4-oxoquinoline-3-carboxylic Acid Hydrochloride A 1.36 g (4.0 mmol) of 5-benzyloxycarbonyl-1-tert-butoxycarbonylamino-5-azaspiro[2.4]heptane (2-b) was dissolved in 50 ml of methanol, and the solution was mixed with 1.2 g of 5% palladium-carbon and stirred under hydrogen atmosphere for 2 hours. The catalyst was removed by filtration through Celite (washed with water), and the filtrate was concentrated under reduced pressure to remove the solvent. The residue was dissolved in DMZ (30 ml). To the solution was added 5-amino-6,7-difluoro-1-[(1R,2S)-2-fluorocyclopropyl]-1,4-dihydro-8-methyl-4-oxoquinoline-3-carboxylic acid (624 mg, 2.0 mmol) and triethylamine (3 ml). The mixture was heated at 140° C. for 15 hours under nitrogen atmosphere, and then concentrated under reduced pressure to remove the solvent. To the residue was added 10% aqueous citric acid solution (50 ml) and extracted with $CHCl_3$ (50 ml×2). The extract was dried over anhydrous sodium sulfate and concentrated under reduced pressure to remave the solvent. To the residue was added conc. HCl (5 ml) and stirred for 1 hour. To the solution was added $H_2O$ (50 ml) and washed with $CHCl_3$ (50 ml×2). The aqueous layer was made pH 12 by adding 1N NaOH, washed with $CHCl_3$ (50 ml×2) and then neutralized to pH 7.4 by 1N HCl. The solution was extracted with $CHCl_3$ (300 ml×5), and the extract was dried over anhydrous sodium sulfate and concentrated under reduced pressure to remove the solvent. The residue was dissolved in 1N HCl (2 ml), and the solution was concentrated to dryness under reduced pressure. Recrystallization of the residue from EtOH gave 29 mg (3.2%) of the title compound.

$^1$H-NMR (400 MHz, $D_2O$) δ: 8.29 (1H, s), 5.10–4.84 (1H, m), 4.01–3.93 (1H, m), 3.83–3.73 (1H, m), 3.67 (1H, d, J=10.74 Hz), 3.52–3.42 (1H, m), 3.33 (1H, d, J=9.77 Hz), 2.38 (3H, s), 2.38–2.30 (1H, m), 2.01–1.91 (1H, m), 1.81–1.71 (1H, m), 1.58–1.45 (1H, m), 1.25–1.12 (1H, m), 0.94–0.88 (1H, m), 0.53–0.47 (1H, m). Elementary analysis for $C_{20}H_{22}F_2N_4O_3 \cdot HCl \cdot \frac{3}{4}H_2O$; Calcd.: C, 52.87; H, 5.43; N, 12.33. Found : C, 52.96, H, 5.36; N, 12.02.

TABLE 1

| Bacteria/Compound (Example No.) | 1 | 4 | 5 | 6 | 7 |
|---|---|---|---|---|---|
| E. coli, NIHJ | ≦0.003 | ≦0.003 | ≦0.003 | ≦0.003 | ≦0.003 |
| S. flexneri, 2A 5503 | ≦0.003 | ≦0.003 | ≦0.003 | ≦0.003 | ≦0.003 |
| Pr. vulgaris, 08601 | 0.006 | 0.013 | 0.013 | ≦0.003 | ≦0.003 |
| Pr. mirabilis, IFO-3849 | 0.013 | 0.025 | 0.05 | 0.013 | 0.013 |
| Ser. marcescens, 10100 | 0.025 | 0.025 | 0.05 | 0.025 | 0.025 |
| Ps. aeruginosa, 32104 | 0.025 | 0.05 | 0.05 | 0.05 | 0.05 |
| Ps. aeruginosa, 32121 | 0.025 | 0.025 | 0.025 | 0.025 | 0.025 |
| Ps. maltophilia, IID-1275 | 0.025 | 0.025 | 0.05 | 0.05 | 0.025 |
| S. aureus, 209P | ≦0.003 | ≦0.003 | ≦0.003 | ≦0.003 | ≦0.003 |
| S. aureus, 87037 | 0.05 | 0.05 | 0.10 | 0.10 | 0.25 |
| S. epidermidis, 56500 | ≦0.003 | ≦0.003 | 0.013 | 0.013 | 0.006 |
| Str. pyogenes, G-36 | 0.013 | 0.013 | 0.05 | 0.013 | 0.006 |
| Str. faeccalis, ATCC-19433 | 0.025 | 0.025 | 0.05 | 0.05 | 0.025 |

What is claimed is:

1. A stereochemically pure ($N_1$-halogenocyclopropyl)-substituted pyridonecarboxylic acid derivative represented by formula (I):

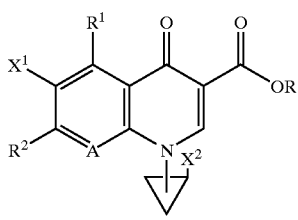

wherein $X^1$ represents a halogen atom;
$X^2$ represents a halogen atom;
$R^1$ represents an amino group, a hydrogen atom, a hydroxyl group or a methyl group;
$R^2$ is a group represented by formula (II):

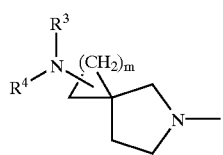

wherein $R^3$ and $R^4$ independently represents a hydrogen atom and m is an integer of 1:
A represents a partial structure of formula (III):

wherein $X^3$ represents a methyl group; and
R represents a hydrogen atom, a phenyl group, an acetoxymethyl group, a pivaloyloxymethyl group, an ethoxycarbonyl group, a choline group, a dimethylaminoethyl group, a 5-indanyl group, a pthalidinyl group, a 5-alkyl-2-oxo-1,3-dioxo-4-ylmethyl group, a 3-acetoxy-2-oxobutyl group, an alkyl group having 1 to 6 carbon atoms, an alkoxymethyl group having 2 to 7 carbonatoms or a phenyl alkyl group composed of alkylene group having 1 to 6 carbon atoms and a phenyl group; or a salt thereof.

2. The compound or a salt thereof according to claim 1, wherein said halogenocyclopropyl group in the formula (I) is (1R,2S)-2-fluorocyclopropyl group.

3. The compound or a salt thereof according to claim 2, wherein $X^1$ is a fluorine atom.

4. A stereochemically pure 7-[1-amino-5-azaspiro[2.4]hetan-5-yl]-6-fluoro-[(1R,2S)-2-fluorocyclopropyl]-1,4-dihydro-8-methyl-4-oxoquinolin-3-carboxylic acid or a salt thereof.

5. A stereochemically pure 5-Amino-7-[1-amino-5-azaspiro[2.4]heptan-5-yl]-6-fluoro-1-[(1R,2S)-2-fluorocyclopropyl]-8-methyl-1,4-dihydro-4-oxoquinoline-3-carboxylic acid or a salt thereof.

6. The compound represented by the following formula, or a salt thereof

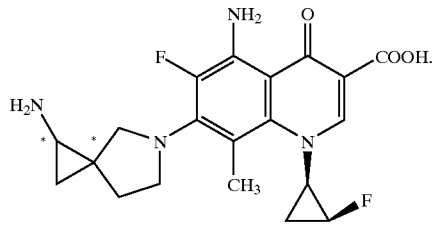

7. The compound represented by the following formula, or a salt thereof

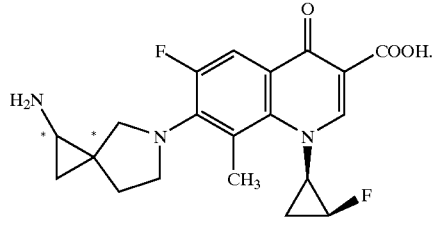

* * * * *